United States Patent
Christopher

(12) United States Patent (10) Patent No.: US 6,631,713 B1
(45) Date of Patent: *Oct. 14, 2003

(54) METHOD AND APPARATUS FOR VENTILATION/OXYGENATION DURING GUIDED INSERTION OF AN ENDOTRACHEAL TUBE

(75) Inventor: Kent L. Christopher, Denver, CO (US)

(73) Assignee: Evergreen Medical Incorporated, Denver, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 09/525,270

(22) Filed: Mar. 14, 2000

Related U.S. Application Data

(63) Continuation-in-part of application No. 09/411,610, filed on Oct. 1, 1999, which is a continuation-in-part of application No. 08/974,864, filed on Nov. 20, 1997, now Pat. No. 5,964,217, which is a continuation of application No. 08/607,332, filed on Feb. 26, 1996, now Pat. No. 5,694,929.

(51) Int. Cl.[7] .............................................. A61M 16/00
(52) U.S. Cl. .......................... 128/200.21; 128/206.28; 128/206.29; 128/207.14
(58) Field of Search ................ 128/200.26, 206.29, 128/207.14, 207.15, 207.16, 206.28, 202.28, 202.29, 203.11

(56) References Cited

U.S. PATENT DOCUMENTS

| | | | |
|---|---|---|---|
| 1,873,160 A | | 8/1932 | Sturtevant |
| 3,556,097 A | * | 1/1971 | Wallace ................ 128/204.18 |
| 3,683,908 A | | 8/1972 | Michael et al. |
| 3,809,079 A | | 5/1974 | Buttaravoli |
| 3,874,377 A | * | 4/1975 | Davidson ............... 128/202.28 |
| 3,948,255 A | * | 4/1976 | Davidson ............... 128/202.28 |
| 4,054,135 A | | 10/1977 | Berman |
| 4,063,913 A | * | 12/1977 | Kippel et al. ............... 55/274 |
| 4,067,331 A | | 1/1978 | Berman |
| 4,068,658 A | | 1/1978 | Berman |
| 4,069,820 A | | 1/1978 | Berman |
| 4,256,099 A | | 3/1981 | Dryden |
| 4,497,318 A | * | 2/1985 | Don Michael ......... 128/202.28 |
| 4,559,940 A | * | 12/1985 | McGinnis ............. 128/206.29 |
| 4,580,556 A | | 4/1986 | Kondur |
| 4,662,367 A | * | 5/1987 | Gore, Jr. ................ 128/202.28 |
| 4,811,730 A | * | 3/1989 | Milano ................... 128/203.11 |

(List continued on next page.)

Primary Examiner—Weilun Lo
Assistant Examiner—Joseph F. Weiss, Jr.
(74) Attorney, Agent, or Firm—Dorr, Carson, Sloan & Birney, P.C.

(57) ABSTRACT

An endotracheal tube can be inserted into a patient's trachea during resuscitation by using a face mask and a curved guide. The guide is inserted through a flexible port in the face mask and has a curved distal portion that extends into the patient's mouth and hypopharynx. The patient is initially resuscitated by supplying a flow of air/oxygen through the mask. For example, a resuscitation bag can be connected to a rotatable ventilation port on the face mask. Alternatively, a resuscitation attachment with an air filter and one-way valve can be removably attached to the ventilation port of the face mask to enable a health care provider to directly resuscitate the patient. An endotracheal tube is inserted over the distal end of a fiber optic probe. Resuscitation, oxygenation, or artificial ventilation continue without interruption while the fiber optic probe and endotracheal tube are inserted through a flexible port at the proximal end of the curve guide and then advanced along the guide into the patient's airway, thereby allowing the physician to carefully guide the fiber optic probe and endotracheal tube to a position past the larynx while resuscitation continues. The fiber optic probe is then removed from within the endotracheal tube and the mask is removed while leaving the endotracheal tube in place within the trachea.

19 Claims, 11 Drawing Sheets

U.S. PATENT DOCUMENTS

| | | | | |
|---|---|---|---|---|
| 4,848,331 A | * | 7/1989 | Northway-Meyer | 128/200.26 |
| 4,892,095 A | * | 1/1990 | Nakhgevany | 128/207.14 |
| 5,005,568 A | * | 4/1991 | Loescher et al. | 128/202.28 |
| 5,197,463 A | * | 3/1993 | Jeshuran | 128/207.14 |
| 5,203,320 A | | 4/1993 | Augustine | |
| 5,277,178 A | * | 1/1994 | Dingley | 128/200.26 |
| 5,295,478 A | * | 3/1994 | Baldwin | 128/203.11 |
| 5,300,033 A | * | 4/1994 | Miller | 604/197 |
| 5,329,921 A | * | 7/1994 | Socaris et al. | 128/207.14 |
| 5,339,805 A | | 8/1994 | Parker | |
| 5,339,808 A | | 8/1994 | Don Michael | |
| 5,348,000 A | | 9/1994 | Teves | |
| 5,404,873 A | * | 4/1995 | Leagre et al. | 128/204.18 |
| 5,501,214 A | * | 3/1996 | Sabo | 128/205.24 |
| 5,511,543 A | * | 4/1996 | Shirley | 128/203.11 |
| 5,694,929 A | * | 12/1997 | Christopher | 128/207.14 |
| 5,735,265 A | * | 4/1998 | Flynn | 128/203.11 |
| 5,771,885 A | * | 6/1998 | Putrello | 128/205.27 |
| 5,964,217 A | * | 10/1999 | Christopher | 128/200.26 |

* cited by examiner

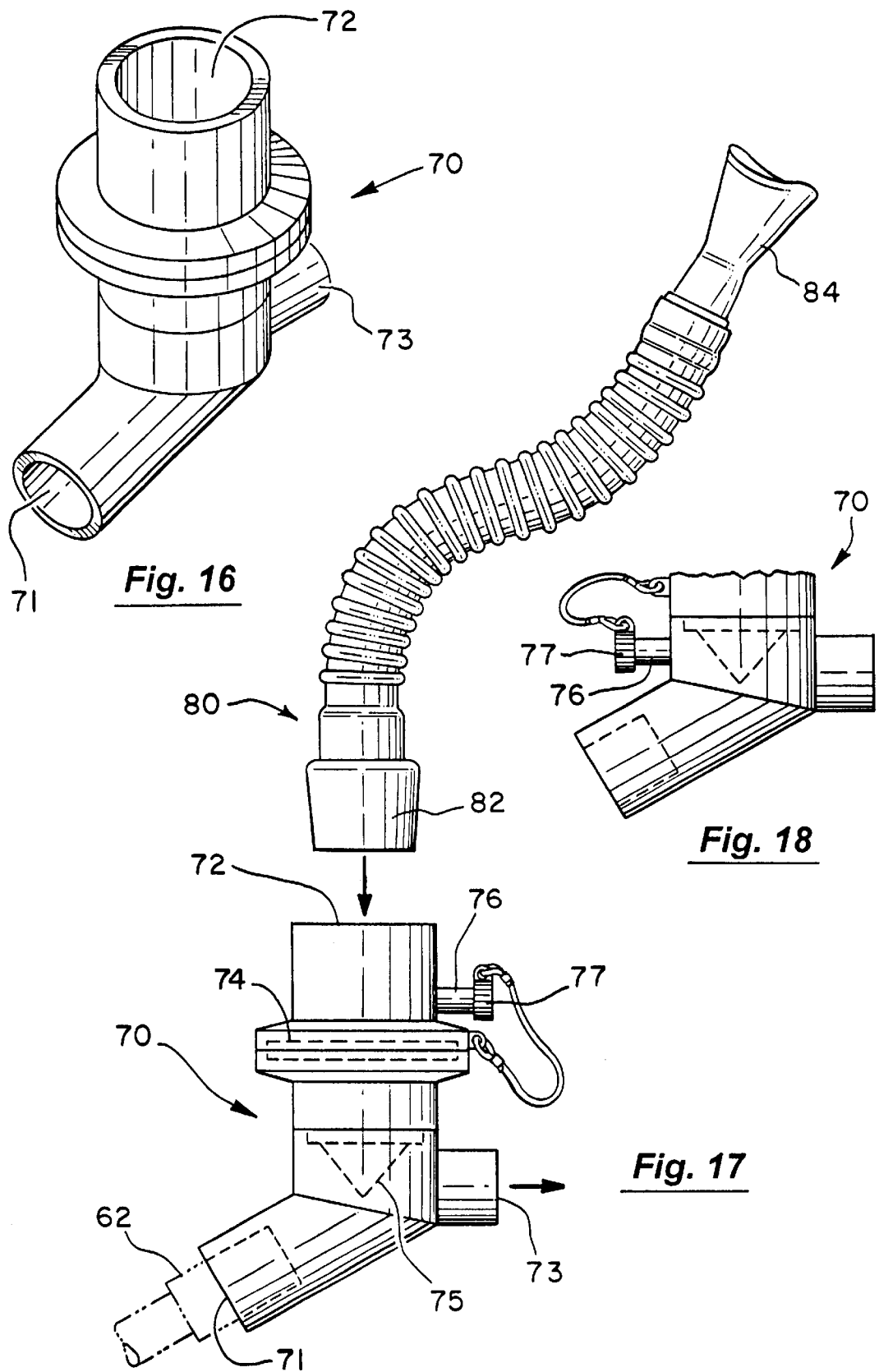

METHOD AND APPARATUS FOR VENTILATION/OXYGENATION DURING GUIDED INSERTION OF AN ENDOTRACHEAL TUBE

RELATED APPLICATIONS

The present application is a continuation-in-part of the Applicant's U.S. patent application Ser. No. 09/411,610, filed on Oct. 1, 1999, which is a continuation-in-part of U.S. patent application Ser. No. 08/974,864, filed on Nov. 20, 1997, now U.S. Pat. No. 5,964,217, issued on Oct. 12, 1999, which is a continuation of U.S. patent application Ser. No. 08/607,332, filed on Feb. 26, 1996, now U.S. Pat. No. 5,694,929, issued on Dec. 9, 1997.

BACKGROUND OF THE INVENTION

1. Field of the Invention

The present invention relates generally to the field of respiratory devices and methods. More specifically, the present invention discloses a method and apparatus for guiding insertion of an endotracheal tube while the patient continues to receive cardiopulmonary resuscitation.

2. Statement of the Problem

In emergency situations involving cardiopulmonary patients or other patients with compromised or arrested breathing, an oral airway is first inserted into the patient's mouth. A face mask is then placed over the patient's mouth and nose. The face mask is connected to an inflatable bag to maintain at least minimal oxygen flow to the lungs in the short term. This process is sometimes referred to as "bagging" the patient. It is suitable for initially stabilizing the patient. In order to breathe more effectively for the patient during cardiopulmonary resuscitation, and to prevent aspiration of stomach contents, an endotracheal tube (or ET tube) is placed into the trachea. Longer-term care usually requires attaching the patient to a ventilator (e.g., by means of the endotracheal tube). The transition from face mask to breathing through the endotracheal tube can be dangerous if insertion of the endotracheal tube takes too long, because the mask and oral airway must be removed and the flow of air/oxygen is interrupted while the endotracheal tube is inserted through the patient's mouth.

The typical conventional approach to making this transition involves discontinuing resuscitation and completely removing the mask and oral airway to expose the mouth. The physician inserts a rigid laryngoscope blade into the patient's mouth to ensure that the patient's airway is open, and then attempts to insert the endotracheal tube through the patient's mouth and into the trachea in the conventional manner. This may require a significant amount of time, particularly if the patient is less than completely cooperative and relaxed, or if the patient's airway has suffered trauma, or the tongue has fallen back to close the airway. The patient may not be breathing during this time, or may not be breathing sufficiently to maintain adequate blood oxygen levels. If the transition process takes more than a few seconds, the physician must temporarily abandon the effort and return to resuscitation by reinserting the oral airway and replacing the face mask. The transition process may have to be repeated several times before the endotracheal tube is successful installed. In addition, the speed with which the transition process must be completed increases the chances of a mistake being made or unnecessary injury to the patient during the intubation procedure.

Endotracheal tubes are also used in semi-emergency situations to ventilate patients with respiratory failure who may be conscious or semi-conscious. The conventional approach requires the patient to lie still while the physician inserts a rigid laryngoscope blade into the patient's mouth and trachea. Delivery of ventilation and/or oxygen is also interrupted during this period. The endotracheal tube is then inserted into place while the laryngoscope blade keeps the patient's airway open. Successful intubation depends on the patient being cooperative and completely relaxed, which unfortunately is often not the case. Even with a cooperative patient, intubation is very uncomfortable and can cause the patient to panic due to the difficulty in breathing during the procedure. This procedure can also result in a choking or gagging response that can cause the patient to regurgitate and aspirate contents from the stomach. One conventional response to these shortcomings has been to sedate the patient during intubation. Tranquilizers make the patient more cooperative and less likely to choke during intubation, but also tend to suppress the patient's breathing and blood pressure. These side effects may be unacceptable when dealing with a patient who already suffers from shallow or irregular breathing or depressed blood pressure. Therefore, a need exists for an improved device to guide insertion of an endotracheal tube and ensure that the patient's airway is open, and that also allows the patient to continue to receive air/oxygen during the insertion process.

A wide variety of devices that combine face masks with tubes for ventilation (e.g., endotracheal tubes) have been used in the past, including the following:

| Inventor | Patent No. | Issue Date |
| --- | --- | --- |
| Teves | 5,348,000 | Sep. 20, 1994 |
| Don Michael | 5,339,808 | Aug. 23, 1994 |
| Jeshuran | 5,197,463 | Mar. 20, 1993 |
| Northway-Meyer | 4,848,331 | Jul. 18, 1989 |
| Kondur | 4,580,556 | Apr. 8, 1986 |
| Donmichael | 4,497,318 | Feb. 5, 1985 |
| Dryden | 4,256,099 | Mar. 17, 1981 |
| Buttaravoli | 3,809,079 | May 7, 1974 |
| Michael et al. | 3,683,908 | Aug. 15, 1972 |

Teves discloses a system for dispensing oxygen or anesthesia via an interchangeable face mask and nasal catheter.

Don Michael discloses a endotracheal-esophageal intubation device that includes a face mask (see, FIG. 2 of the Don Michael patent).

Jeshuran shows an anesthesia mask 28 that is initially placed over the patient's mouth and nose as shown in FIG. 7 of the Jeshuran patent. A fiber optic 40 is inserted through an endotracheal tube, and then through an opening in a two-piece core 84, 86, as shown in FIG. 9 of the Jeshuran patent. The fiber optic 40 is advanced into the trachea. The head 96 is then unscrewed and the core segments 84, 86 are disassembled to allow the endotracheal tube to be inserted through the mask, as shown in FIG. 2 of the Jeshuran patent. The fiber optic 40 serves as a guide for insertion of the endotracheal tube 46. The fiber optic 40 is then withdrawn and the endotracheal tube cuff 136 is inflated, as shown in FIG. 8 of the Jeshuran patent. However, Jeshuran does not show a curved guide to direct insertion of the fiber optic probe. The physician is faced with the problem of navigating the fiber optic probe past the patient's tongue and along the airway.

Northway-Meyer discloses a device for pulmonary ventilation concurrent with fiber optic examination of the respiratory tract and tracheal intubation. In particular, Northway-Meyer discloses a face mask with a plurality of ports for ventilation and intubation of the patient, and curved guide for advancing an endotracheal tube.

Kondur discloses another example of an adapter 10 that allows insertion of an endotracheal tube 40 through the face mask 50 and nose of the patient. Here again, no curved guide is provided.

Donmichael discloses an esophageal obturator for blocking aspiration of stomach fluids while the face mask is being used for ventilating the lungs.

Dryden discloses a two-tube resuscitation system. One tube is used to supply air to the trachea, while the other tube is used for aspiration or administering medication.

Buttaravoli discloses a resuscitator having a face mask 11 with a curved tube 15 for supplying air to the patient's airway.

Michael et al. disclose an apparatus for sealing a patient's esophagus and providing artificial respiration. The apparatus includes a mouth shield 14 and a curved main tube 10.

In addition, the prior art includes several references involving intubating pharyngeal airways that have a curved central tubular member, including the following:

| Inventor | Patent No. | Issue Date |
|---|---|---|
| Parker | 5,339,805 | Aug. 23, 1994 |
| Augustine | 5,203,320 | Apr. 20, 1993 |
| Berman | 4,069,820 | Jan. 24, 1978 |
| Berman | 4,068,658 | Jan. 17, 1978 |
| Berman | 4,067,331 | Jan. 10, 1978 |
| Berman | 4,054,135 | Oct. 18, 1977 |

Parker discloses a curved guide for intubation of a patient's trachea or suctioning of the hypopharnyx or esophagus.

Augustine discloses a tracheal intubation guide with a curved forward end.

The Berman patents show an intubating pharyngeal airway having a side access for passage of a tube. The side opening can be expanded or closed by means of either a hinge on the opposite side wall of the tube or by a cap.

3. Solution to the Problem

None of the prior art references uncovered in the search show a face mask that incorporates a port and a curved guide for directing a fiber optic probe and endotracheal tube along the patient's airway while resuscitation, cardiopulmonary resuscitation, artificial mask breathing, or oxygenation continues.

After the distal end of the fiber optic probe has guided the endotracheal tube past the larynx into the trachea, the fiber optic probe is withdrawn and the endotracheal tube can be used to more effectively "bag" the patient, or the patient can be connected to an external ventilator.

This system allows the endotracheal tube to be inserted and connected to a ventilator without interrupting resuscitation or oxygenation of the patient via the face mask. In addition, the curved guide greatly simplifies insertion of the fiber optic probe and endotracheal tube by providing direction and maintaining an open passageway past the patient's tongue and into the hypopharynx. The flow of air/oxygen supplied by the resuscitation bag tends to inflate the patient's mouth and airway, and thus also helps to maintain a passageway and visualization for the fiber optic probe and endotracheal tube.

SUMMARY OF THE INVENTION

This invention provides a method and apparatus for guiding insertion of an endotracheal tube into a patient's trachea during resuscitation by using a face mask and a curved guide. The guide is inserted through a flexible port in the face mask and has a curved distal portion that extends into the patient's mouth and hypopharynx. The patient is initially resuscitated by supplying a flow of air/oxygen through the mask. For example, a resuscitation bag can be connected to a rotatable ventilation port on the face mask. Alternatively, a resuscitation attachment with an air filter and one-way valve can be removably attached to the ventilation port of the face mask to enable a health care provider to directly resuscitate the patient. An endotracheal tube is inserted over the distal end of a fiber optic probe. Resuscitation, oxygenation, or artificial ventilation continue without interruption while the fiber optic probe and endotracheal tube are inserted through a flexible port at the proximal end of the guide and then advanced along the guide into the patient's airway. The direction of the distal tip of the fiber optic probe can be controlled by the physician. This allows the physician to carefully guide the fiber optic probe and endotracheal tube to a position past the larynx while resuscitation continues. The fiber optic probe is then removed from within the endotracheal tube and the mask is removed while leaving the endotracheal tube in place within the trachea. The cuff on the endotracheal tube is inflated and a ventilator is connected to the proximal end of the endotracheal tube to ventilate the patient. Alternatively, the patient can be manually ventilated by connecting a resuscitation bag to the proximal end of the endotracheal tube.

A primary object of the present invention is to provide a method and apparatus for guiding insertion of an endotracheal tube that does not require interruption of the resuscitation process.

Another object of the present invention is to provide a method and apparatus for improving insertion of an endotracheal tube by helping to keep the patient's airway open, and also allowing the physician to guide the insertion process via the fiber optic probe.

Another object of the present invention is to provide a method and apparatus for instilling local anesthetic into the patient's airway and suctioning excess secretions prior to insertion of the endotracheal tube.

Another object of the present invention is to provide a method and apparatus for guiding insertion of an endotracheal tube that lessens the risk of injury and reduces patient discomfort.

Yet another object of the present invention is to provide a device that enables the physician to instill anesthetic and/or suction secretions from the patient's mouth and airway as the device is inserted.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 16 is a front perspective view of a removable resuscitation attachment 70 that can be connected to the ventilation port 62 of the face mask assembly.

FIG. 17 is a side view of the resuscitation attachment 70 and flexible tubing 80.

FIG. 18 is a detail side view of an alternative embodiment of the resuscitation attachment 70 in which the location of the oxygen port 76 has been placed below the filter and one-way valve.

DETAILED DESCRIPTION OF THE INVENTION

Figures 1, 2:
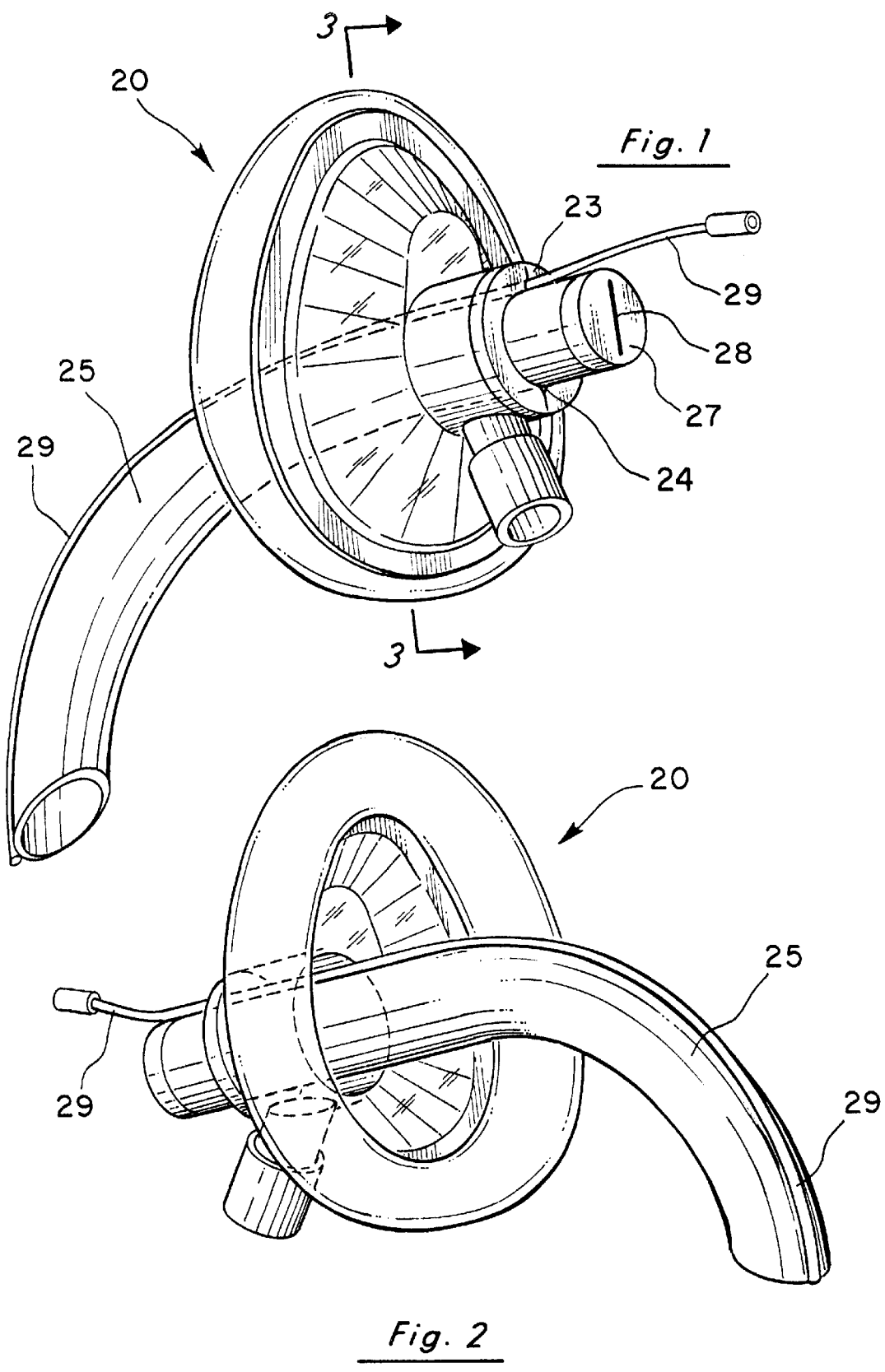
FIG. 1 is a front perspective view of the face mask assembly, including the port 23 and curved guide 25.
FIG. 2 is a rear perspective view of the mask assembly corresponding to FIG. 1.
Figure 3:
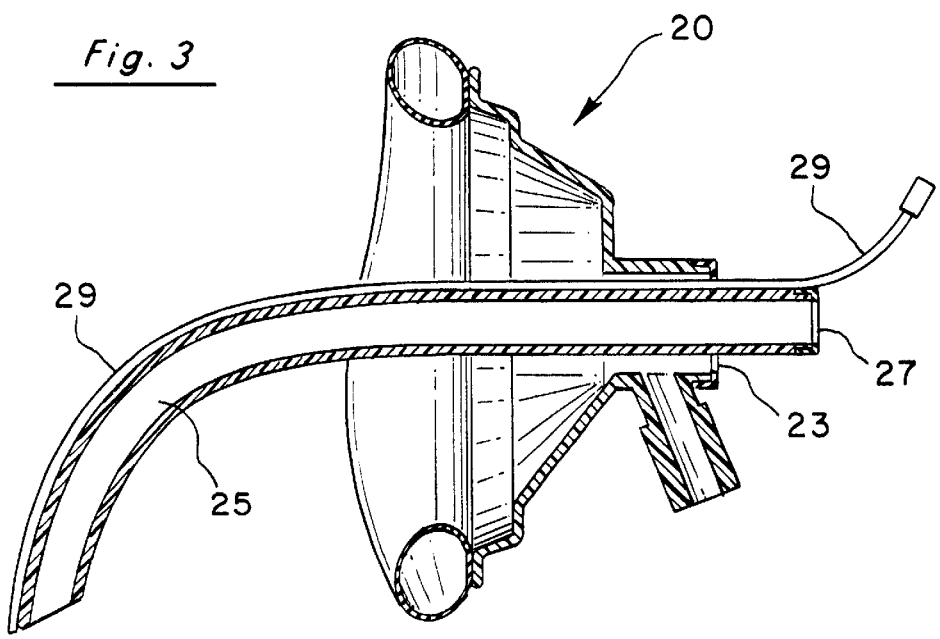
FIG. 3 is a cross-sectional view of the mask assembly corresponding to FIG. 1.
Figure 5:
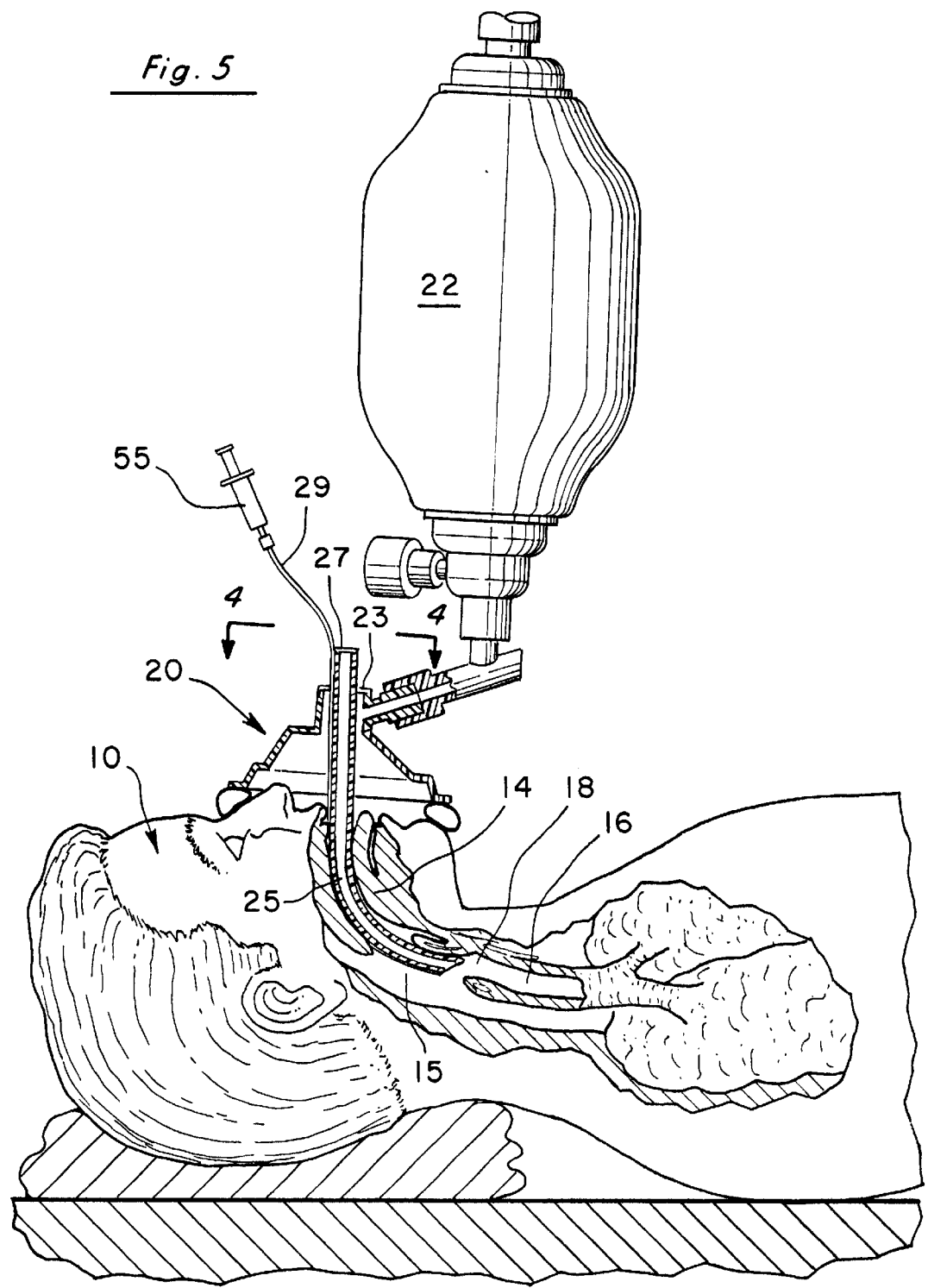
FIG. 5 is a cross-sectional view of the mouth and airway of a patient after the mask 20 has been initially placed over the patient's mouth and nose with the curved guide 25 extending into the mouth, over the tongue 14, and into the hypopharynx 15.

Turning to FIGS. 1 and 2, front and rear perspective views of the present invention are illustrated. A corresponding cross-sectional view is shown in FIG. 3. The face mask 20 is adapted to fit over the patient's mouth and nose for resuscitation of the patient 10 as shown in FIG. 5. The mask 20 has a low profile and is made of an elastic material, such as rubber or flexible plastic, to allow the mask to conform to the contours of the patient's face and create a more air-tight seal around the mouth and nose.

Figure 4:
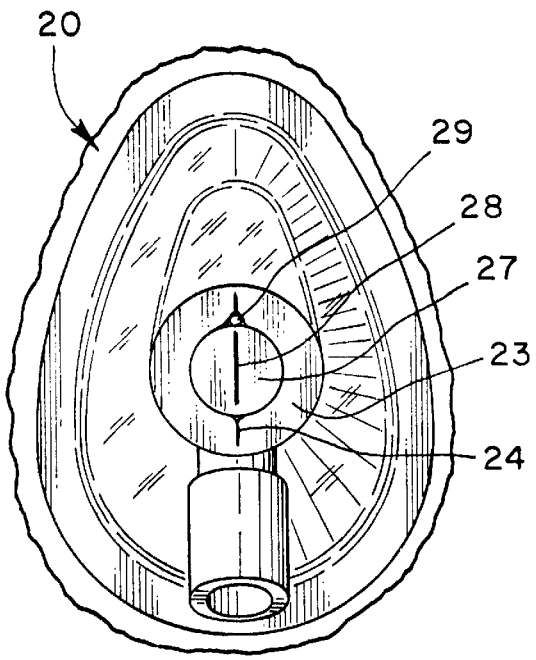
FIG. 4 is a front view of the face mask port 23 showing the stretchable opening 24 closed.

The face mask 20 includes a resealable port 23. In the preferred embodiment, the face mask port 23 consists of a flexible, elastic membrane having a stretchable opening 24 with dimensions large enough to allow a curved guide 25 to pass through the face mask port 23. For example, this elastic membrane can be made of rubber with slot or hole forming an opening 24, as shown in FIG. 4.

As depicted in FIG. 5, the curved guide 25 can be readily inserted through the face mask port 23 while maintaining a substantially air-tight seal around the guide 25 to prevent gas from escaping from within the face mask 20. The guide 25 is generally tubular and includes a resealable port 27 at its proximal end. For example, the guide port 27 can be made of a flexible, elastic membrane having a stretchable slot or opening 28 with dimensions large enough to allow an endotracheal tube to pass through the guide port 27. The guide 25 extends posteriorly through the face mask 20 and has a curved distal portion that is inserted into the patient's mouth and hypopharynx 15 as the face mask 20 is placed over the patient's mouth. The distal portion of the curved guide 25 generally follows the profile of a typical patient's airway through the mouth, over the tongue 14, and into the hypopharynx 15 just above the opening to the trachea 16. The guide 25 is shaped to prevent the patient's tongue 14 and collapsible pharynx from obstructing access to the trachea 16, while also defining a channel for later insertion of an endotracheal tube. The guide 25 is typically made of plastic with sufficient strength and rigidity to keep the patient's teeth apart and prevent the patient from biting down on the endotracheal tube. The face mask port 23 allows the guide 25 to slide relative to the face mask 20, and also allows a limited range of rotation of the guide 25. This flexibility allows the guide 25 to accommodate a wide range of patient sizes and conditions.

In the preferred embodiment, the guide 25 is equipped with small tube 29 bonded to the exterior of the guide 25 that extends along the length of the guide 25 to its distal end. This tube 29 can be used to suction secretions from the patient's mouth and airway as the guide 25 is advanced. Alternatively a syringe 55 containing a local anesthetic (e.g., lidocaine or xylocaine) can be connected to the proximal end of the tube 29 to squirt anesthetic as the guide 25 is insert through the patient's mouth and into the hypopharynx 15, as illustrated in FIG. 5. If squirted with sufficient force, the anesthetic can be carried as far as the larynx 18 to deaden any discomfort associated with insertion of the endotracheal tube 40. Alternatively, the physician can squirt anesthetic directly down the main passageway of the guide 25. The main passageway can also be used for suctioning secretions from the patient's mouth and airway.

The patient is initially resuscitated by supplying a flow of air/oxygen through the mask. For example, the flow of air can be supplied by a resuscitation bag 22 attached to the mask 20 that is manually squeezed periodically to simulate natural breathing. However, other conventional air/oxygen supplies for resuscitation could be substituted at the connector for the face mask 20. In the preferred embodiment, the flow of oxygen/air from the resuscitation bag 22 is directed around the exterior of the curved guide 25. This tends to inflate the patient's mouth and airway, which distends the collapsible tissues, and thereby makes visualization and insertion of the endotracheal tube 40 easier.

Figure 7:
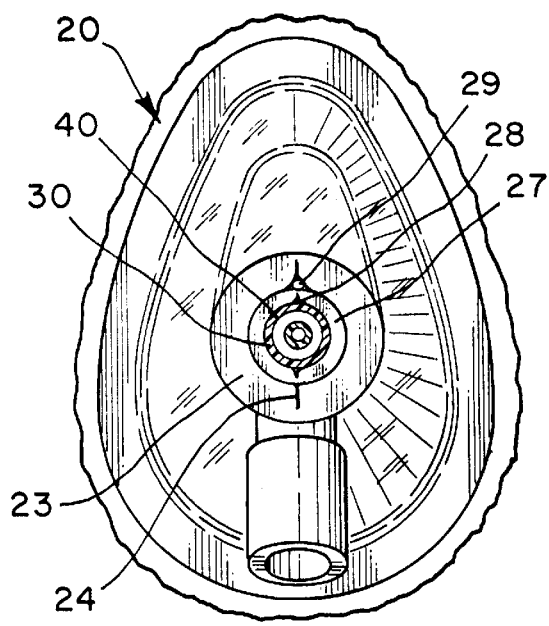
FIG. 7 is a front view of the mask port 23 corresponding to FIG. 6 showing the fiber optic probe 30 and endotracheal tube 40 in cross-section.
Figure 6:
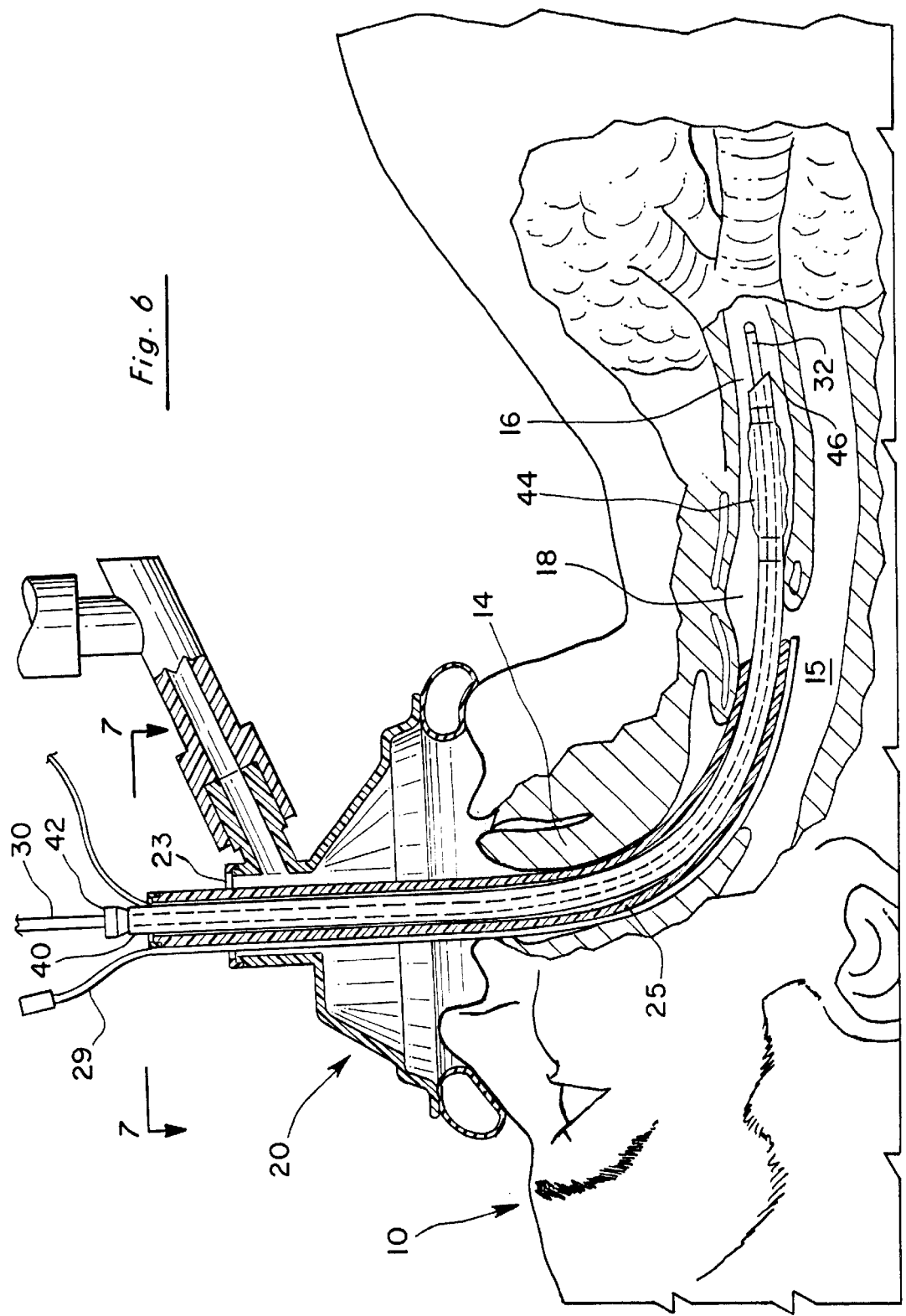
FIG. 6 is a cross-sectional view of the mouth and airway of the patient corresponding to FIG. 5 after the fiber optic probe 30 and endotracheal tube 40 have been inserted through the face mask port 23 and advanced along the curved guide 25 to a position below the larynx 18.

After the patient's conditioned has been stabilized to some degree during initial resuscitation, an endotracheal tube 40 is inserted over a fiber optic probe 30. The fiber optic probe 30 and endotracheal tube 40 are then inserted through the guide port 27 and along the guide 25 to a position within the trachea 16 past the larynx 18 while resuscitation continues, as illustrated in FIG. 6. The opening 28 in the flexible membrane stretches to allow the endotracheal tube 40 and fiber optic probe 30 to pass through the guide port 27, but maintains a sufficiently tight fit around the endotracheal tube 40 to prevent the escape of gas from within the mask 20, as shown in the front view of the face mask provided in FIG. 7.

The fiber optic probe 30 allows the physician to view within the patient's mouth and trachea 16 during insertion. The physician can also remotely manipulate the direction of the probe tip 32 to control the direction of the fiber optic probe 30. This minimizes patient discomfort and risk of injury to the patient. The small size of the fiber optic probe 30 also allows the physician to thread the fiber optic probe 30 through relatively constricted areas within the airway, such as the larynx 18. Most importantly, the fiber optic probe 30 and endotracheal tube 40 do not interfere with ongoing resuscitation of the patient.

The distal end 46 of the endotracheal tube 40 can beveled as illustrated most clearly in FIG. 6. Experience has shown that injury to the larynx 18 can be reduced by spinning the endotracheal tube 40 as it is advanced. The beveled end tends to keep the endotracheal tube 40 centered as it is passes through the vocal cords. Injury to the lining of the mouth and trachea can be reduced by using an endotracheal tube 40 made of a material having a low coefficient of friction, such as silicone. Bivona Medical Technologies of Gary, Ind., markets a line of endotracheal tubes made of silicone with a helical reinforcing wire.

Figure 8:
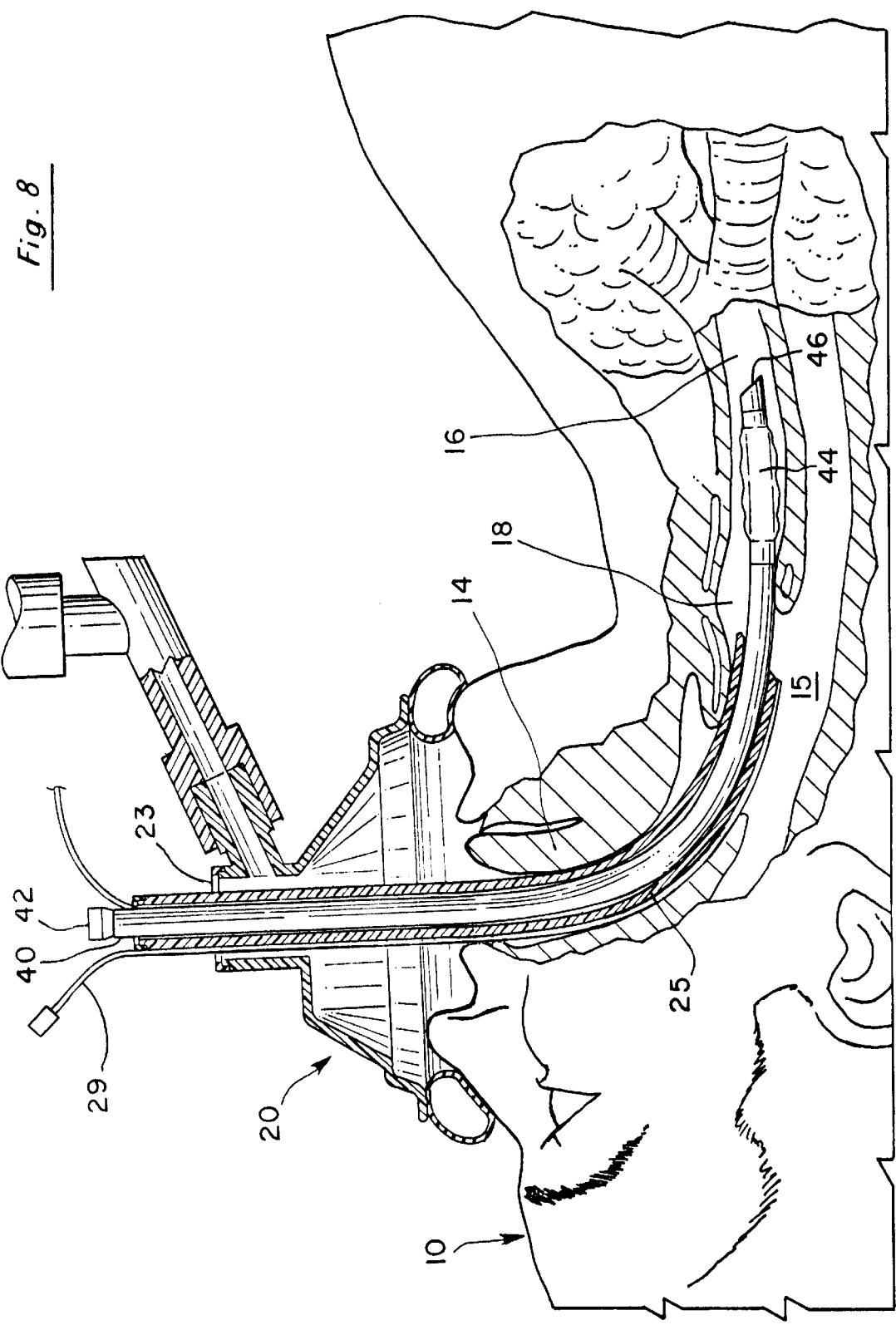
FIG. 8 is a cross-sectional view of the mouth and airway of the patient corresponding to FIG. 5 after the fiber optic probe 30 has been removed from within the endotracheal tube 40.
Figure 9:
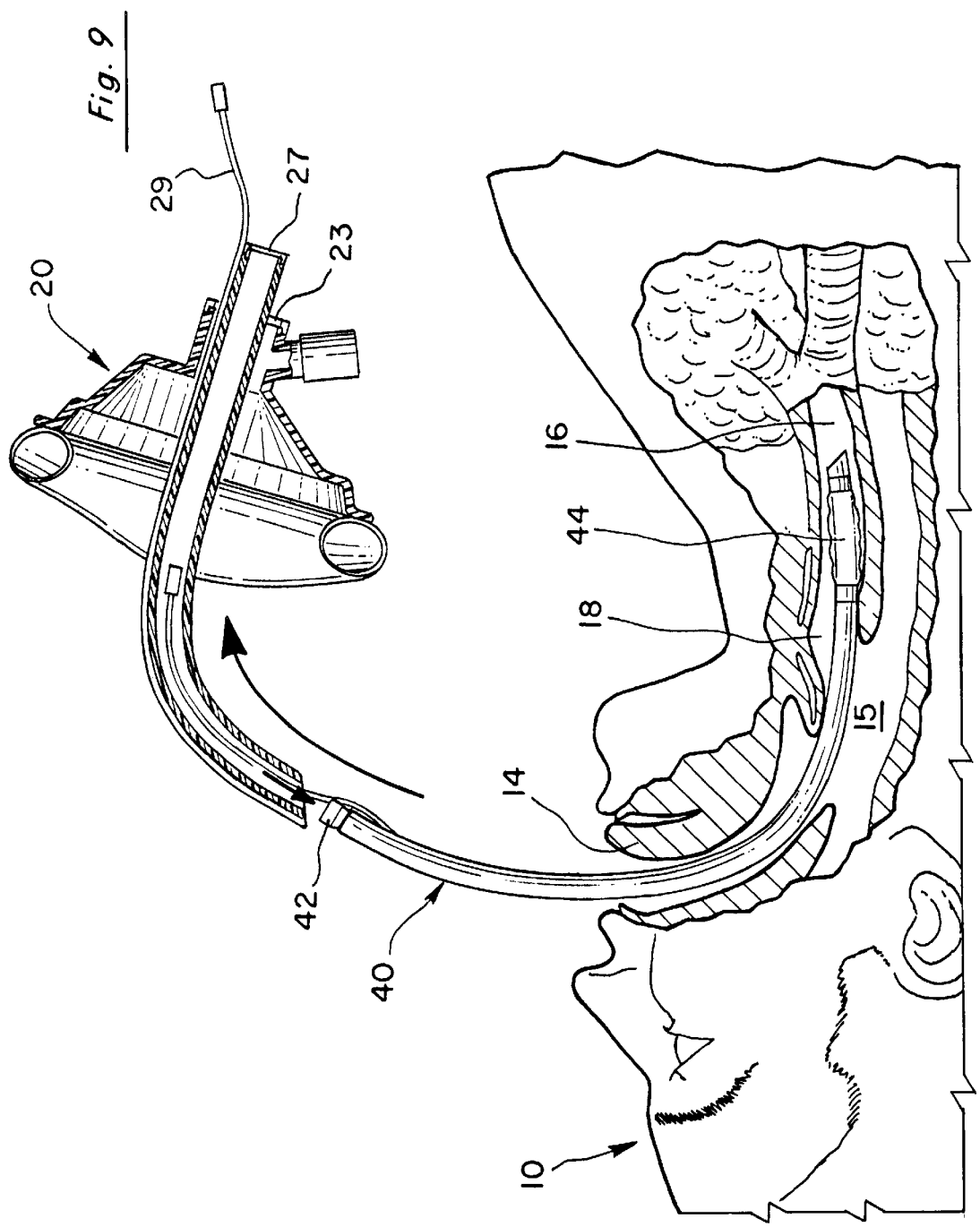
FIG. 9 is a cross-sectional view of the mouth and airway of the patient corresponding to FIG. 5 showing the face mask 20 being removed while the endotracheal tube 40 remains in place.

After the endotracheal tube 40 has been inserted, the fiber optic probe 30 is removed from within the endotracheal tube 40 through the proximal end of the endotracheal tube 40, as depicted in FIG. 8. The face mask 20 and guide 25 can then be removed while leaving the endotracheal tube 40 in place within the trachea 16, as shown in FIG. 9. The opening 28 in the flexible port 27 allows the face mask 20 and guide 25 to be withdrawn over the connector 42 at the proximal end of the endotracheal tube 40 with minimal effort and dislocation of the endotracheal tube 40. The position of the endotracheal tube 40 can be stabilized while the mask 20 is removed by manually gripping the proximal end of the endotracheal tube 40 and gradually urging it through the port 27 as the mask 20 is lifted from the patient's face. The physician can then reach under the face mask 20 to grip the endotracheal tube 40 after the mask 20 has been lifted sufficiently to allow access.

Alternatively, the face mask 20 can be removed while leaving the guide 25 in place to serve as an oral airway and to protect the endotracheal tube 40 from being bitten by the patient's teeth. After the face mask 20 has been removed, the endotracheal tube is taped to the patient's face, or held in place by some other suitable means for attachment.

Figure 10:
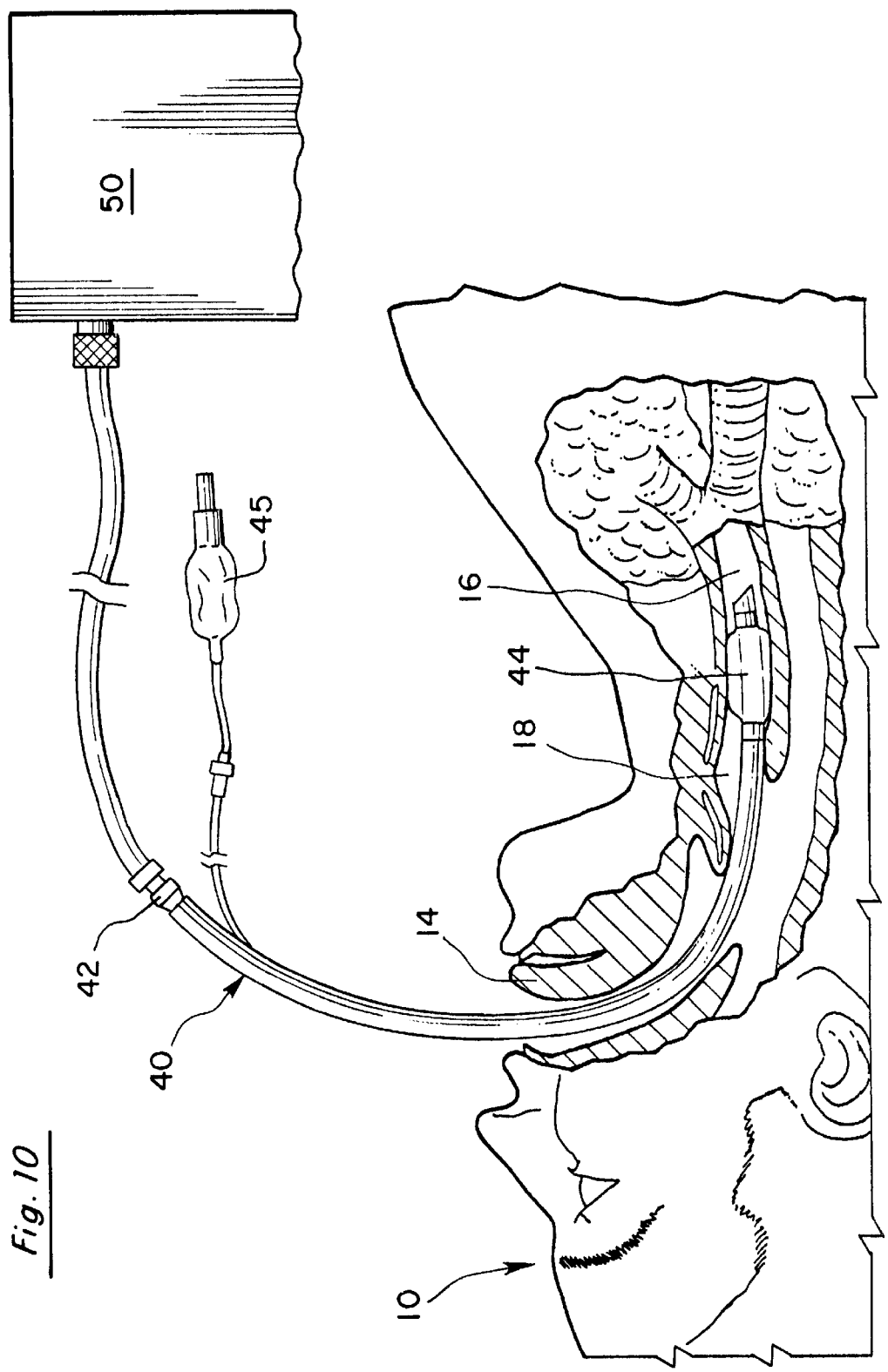
FIG. 10 is a cross-sectional view of the mouth and airway of the patient corresponding to FIG. 5 after the mask 20 has been removed, the endotracheal tube cuff 44 has been inflated, and a ventilator 50 has been connected to the endotracheal tube 40.

The cuff 44 at the distal end 46 of the endotracheal tube 40 is then inflated through the port valve 45 to block the trachea 16. An external ventilator 50 can be attached to the connector 42 at the proximal end of the endotracheal tube 40, as shown in FIG. 10. The patient can then be mechanically ventilated in the conventional manner via the endotracheal tube 40. Alternatively, the patient can be manually ventilated by attaching a resuscitation bag to the connector 42 at the proximal end of the endotracheal tube.

Figure 11:
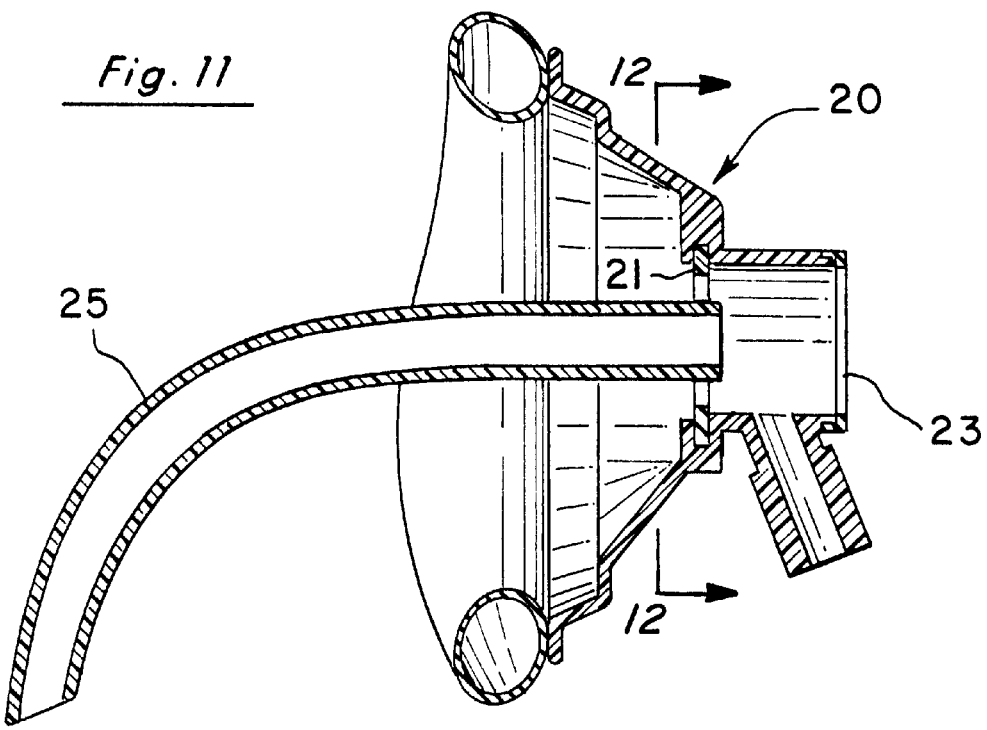
FIG. 11 is a cross-sectional view of the face mask 20 and guide 25 in an alternative embodiment in which the curved guide 25 is configured as a oral airway that engages the posterior surface of the mask 20 surrounding the face mask port 23.
Figure 12:
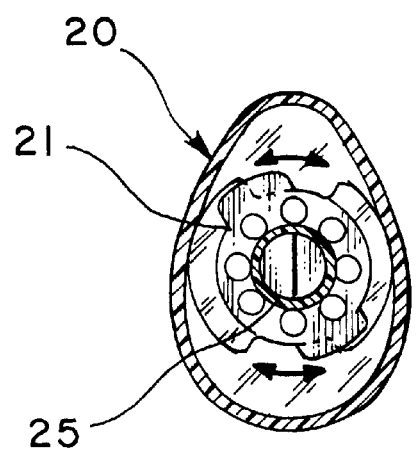
FIG. 12 is a rear detail view of locking mechanism 21 used to engage the curved guide 25 to the posterior surface of the mask 20.

It should be understood that the guide 25 and mask 20 can have any number of possible embodiments. The embodiment shown in the drawings uses a guide 25 that extends through an elastic port 23 in the face mask 20. This allows a limited range of motion between the guide 25 and mask 20 to make insertion of the guide easier, but requires two elastic ports 23 and 28. Alternatively, the guide 25 and mask 20 could be fabricated as two separate pieces that engage one another, as illustrated in FIG. 11. This eliminates the need for the guide port 27. In this embodiment, the guide 25 is separately inserted into the mouth, similar to a conventional oral airway. The mask 20 is then placed over the patient's mouth and nose so that the proximal end of the guide 25 engages a corresponding opening in the posterior face of the mask 20 to provide a relatively continuous passageway for insertion of the fiber optic probe 30 and endotracheal tube 40 through the face mask port 23 and along the guide 25. FIG. 12 provides a rear detail view of the locking mechanism 21 used to engage the guide 25 to the posterior face of the mask 20. The guide 25 can be readily disengaged by rotating it slightly relative to the face mask 20. After the endotracheal tube 40 has been inserted, the mask 20 is removed while leaving the guide 25 in place within the patient's mouth. The guide 25 remains around the endotracheal tube 40 and protects it from being bitten or crimped by the patient's teeth.

The guide 25 can consist of a tubular member as shown in the drawings. Alternatively, the distal portion of the guide 25 can have a U-shaped cross-section. The guide 25 can be molded from a suitable plastic material having a relatively low coefficient of friction to minimize irritation to the lining of mouth and trachea and to minimize resistance to insertion of the endotracheal tube 40 along the guide. Friction can be further reduced by applying a slippery coating to both the exterior and interior surfaces of the guide 25. A slippery coating can also be applied to the endotracheal tube to minimize friction between the endotracheal tube and the guide.

All of the components necessary to practice the present invention can be readily packaged as a kit for use in emergency rooms and intensive care units. The kit is sufficiently compact and inexpensive that it can be stocked on resuscitation carts widely used in hospitals, and carried in ambulances for use by emergency medical technicians in the field. The fiber optic probe can be operated using a battery-powered light source. The oxygen supply for the hospital or ambulance can be connected to the face mask 20 for resuscitation or to provide a flow of gas to the ventilator 50. The tube 29 extending along the guide 25 can also be connected to the suction system provided by the hospital or ambulance, if necessary.

Figure 13:
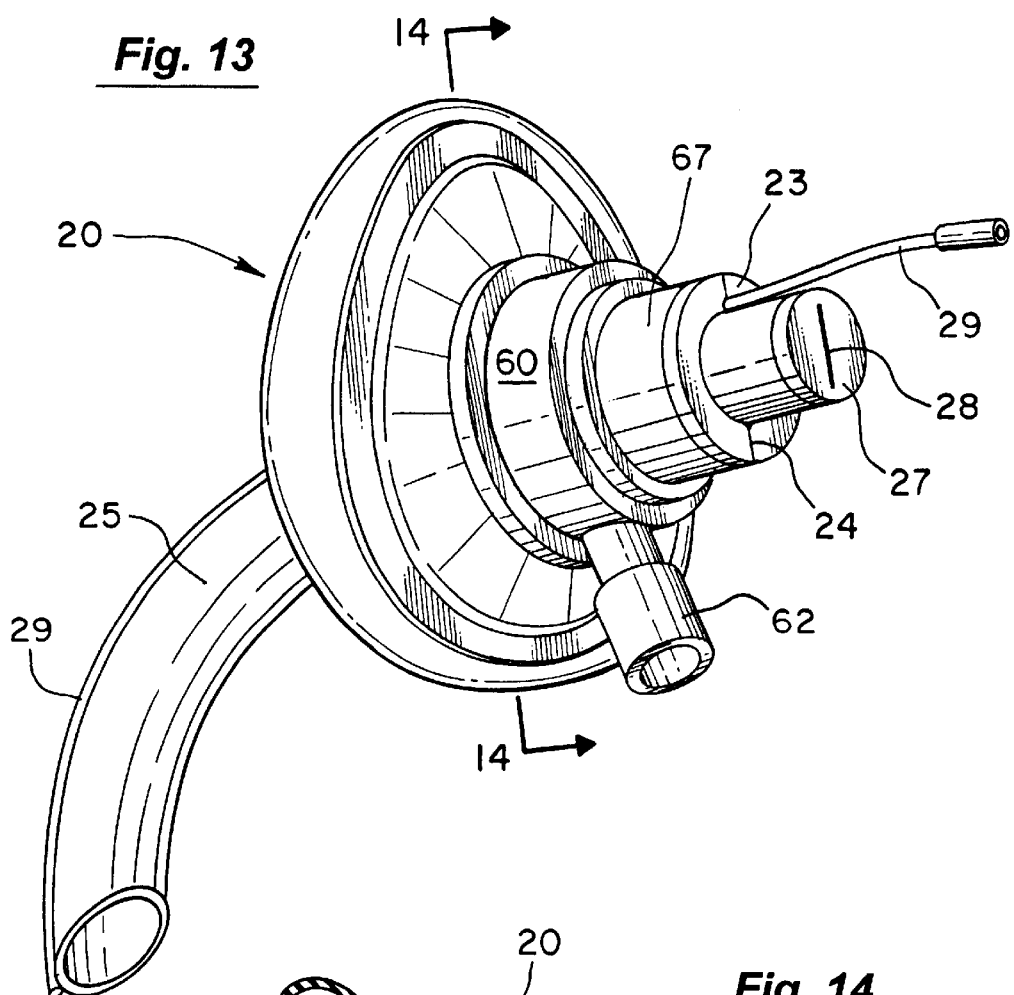
FIG. 13 is a front perspective view of an alternative embodiment of the face mask assembly.
Figure 14:
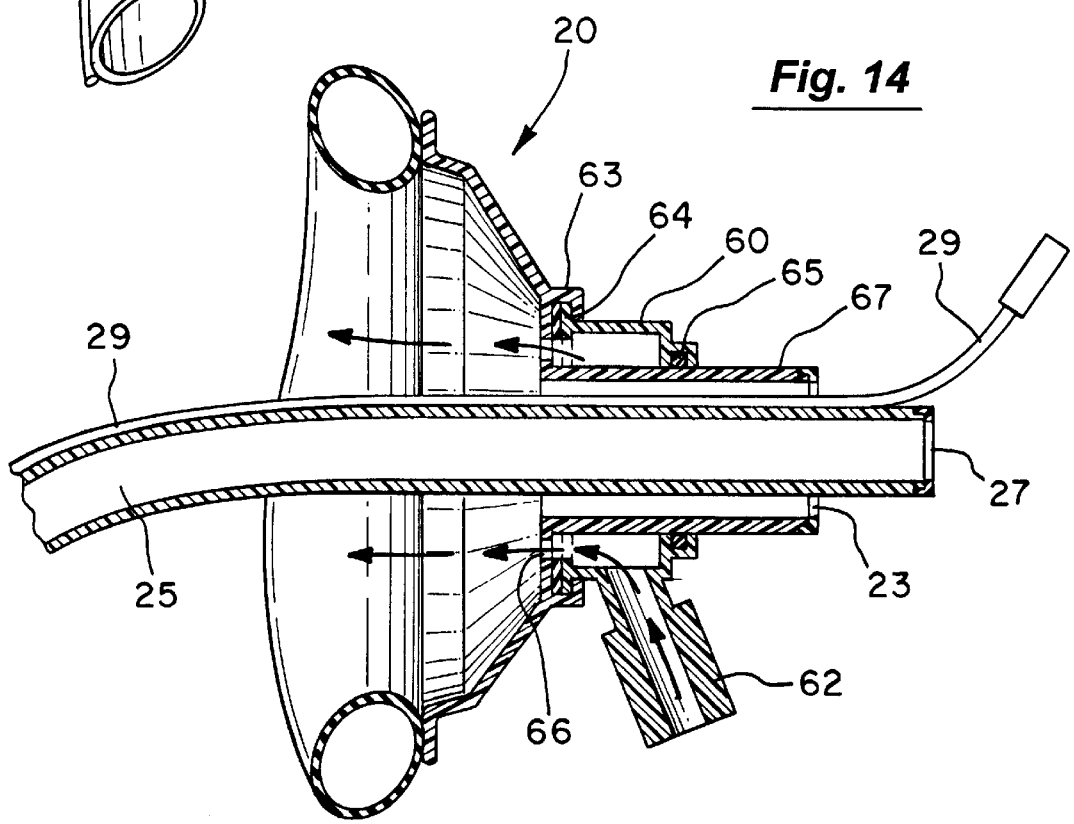
FIG. 14 is a cross-sectional view of the mask assembly corresponding to FIG. 13.
Figure 15:
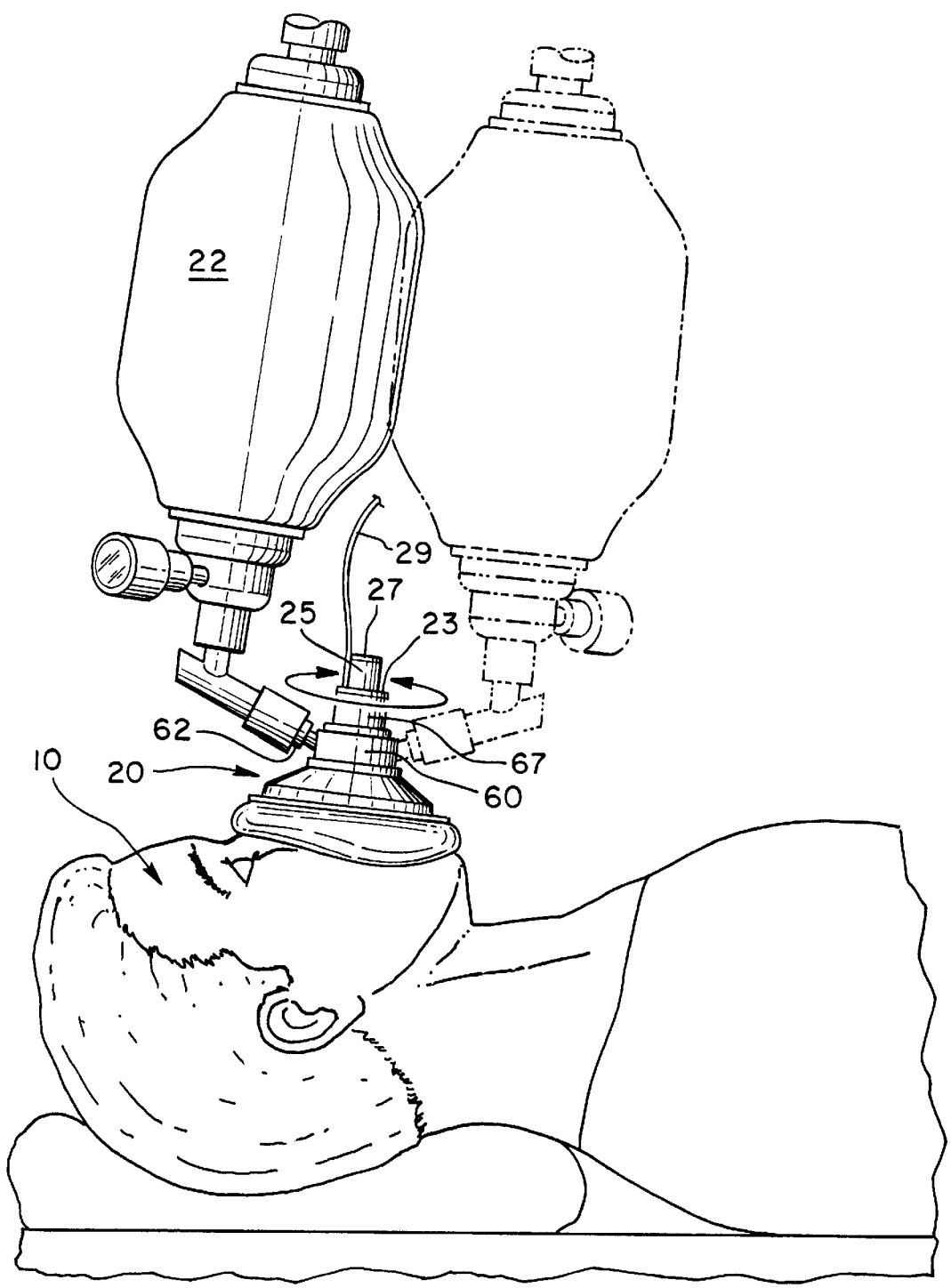
FIG. 15 is a side elevational view corresponding to FIGS. 13 and 14 showing the mask assembly 20 placed over the patient's mouth and nose.

Rotatable Ventilation Port. FIG. 13 is a front perspective view of an alternative embodiment of the face mask assembly with a rotating ventilation port. FIG. 14 shows a cross-sectional view of the mask assembly corresponding to FIG. 13. FIG. 15 is a side elevational view showing the mask assembly 20 placed over the patient's mouth and nose.

In contrast, the embodiment of the present invention illustrated in FIGS. 1–12 has a fixed ventilation port for connecting a resuscitation bag 22 or other source of air/oxygen to the face mask 20. This limitation may present a significant problem in emergency situations in which only limited access to the patient is available, or in which the patient cannot be readily moved. Similar problems can also occur in a hospital setting, due to the patient's position in bed, or surrounding medical equipment that can limit access to the patient from one side or the other.

Returning to FIGS. 13–15, the mask assembly includes a rotatable annular ventilation collar 60 with a ventilation port 62 that can be connected to a conventional respiration bag 22 or other air/oxygen source to ventilate the patient. The ventilation collar 60 allows the ventilation port 62 to be freely rotated to any desired orientation about the face mask port 23.

Air from the resuscitation bag 22 flows through the ventilation port 62 and into the annular ventilation collar 60. It then flows through a plurality of small ventilation holes 66 in the mask 20 beneath the annular ventilation collar 60 into the patient's mouth and nose. The resuscitation bag 22 is typically used to initially resuscitate the patient, and to provide short-term ventilation until the endotracheal tube is in place and connected to a ventilator. After the patient has been intubated and connected to the ventilator, the resuscitation bag 22 can be removed. If needed, the resuscitation bag 22 can reconnected to the ventilation port 62 to supplement the flow provided by the ventilator.

In particular, the mask 20 includes a raised cylindrical flange 63 that engages a corresponding flange 64 extending around the base of the annular ventilation collar 60 to provide a rotatable, but generally air-tight seal between the mask 20 and the ventilation collar 60. A tubular member 67 extends upward from the surface of the mask 20 beneath the ventilation collar 60, and passes through the central opening in the annular ventilation collar 60. An O-ring 65 provides a rotatable, air-tight seal between the outer surface of the tubular member 67 and the ventilation collar 60, and also serves to retain the ventilation collar in place on the mask assembly 20.

A resealable face mask port 23 is provided at the upper opening of the tubular member 67, so that a curved guide 25 can be removably inserted through the face mask port 23 and into the patient's mouth and hypopharynx 15, as illustrated in FIG. 5. When the face mask port 23 is not in use (e.g., during initial resuscitation of a patient using the resuscitation bag 22), the face mask port 23 should remain sealed to prevent gas from escaping from the face mask 20. For example, the face mask port 23 can be a flexible membrane that has a stretchable opening to receive the guide 25. When the guide 25 is not inserted through the face mask port 23, the flexible membrane retracts to substantially seal the opening and prevent gas from escaping from the face mask port 23, as previously discussed. Alternatively, the face mask port 23 can be equipped with a removable cap to seal the port with it is not in use.

Resuscitation Attachment. FIG. 16 is a perspective view of a removable resuscitation attachment 70 that can used in place of the the resuscitation bag 22 for mouth-to-mask resuscitation by the rescue person. In a hospital setting, the first person responding to a patient in need of resuscitation typically activates an alarm to summon a resuscitation team, and then immediately begins mouth-to-mouth resuscitation of the patient until the resusciation team arrives. To help minimize the risk of contamination, many hospitals equip each hospital bed with a face mask having a ventilation port for mouth-to-mask resuscitation. This type of face mask is also commonly provided for use by police and firemen with little medical training. When the resuscitation team arrives, this face mask is generally replaced with a system consisting of a second face mask, an oral airway, and a resuscitation bag. Since the patient usually requires intubation, this second face mask must be removed while an endotracheal tube is inserted into the patient's airway and the patient is connected to a ventilator. Each of these transitions entails an interruption in on-going resuscitation efforts, which can be detrimental to the patient. According to the American Heart Association, a period in excess of 30 seconds without breathing or circulation can cause irreversible brain and heart damage.

In addition, the most common types of face masks used for initial resuscitation at the patient's bed do not include a guide or oral airway to keep the patient's airway open. As a result, initial efforts at manual resuscitation using the first face mask may be partially or completely ineffective, until the resuscitation team arrives and replaces the first face mask with a second face mask and a separate airway device used to keep the patient's airway open.

In contrast to the conventional approach practiced in many hospitals, as described above, the present invention allows the same face mask to be used throughout the entire process without interrupting resuscitation. In addition, the present invention includes a face mask with a curved guide that can be inserted into the patient's airway to maintain patency during the first effort to resuscitate the patient before the resuscitation team arrives.

Returning to FIG. 16, the resuscitation attachment 70 has an output port 71 that can be removably connected to the ventilation port 62 of the face mask 20. The healthcare provider administers mouth-to-mask resuscitation to the patient via the resuscitation attachment 70 and face mask 20.

The resuscitation attachment 70 includes an air filter 74 across the flow path between the input port 72 and output port 71, to help prevent the exchange of contaminants between the healthcare provider and patient. A one-way valve 75 (e.g., a duckbill valve) directs any backflow of air or contaminated fluids from the face mask 20 to the exhaust port 73, and thereby serves to further protect the healthcare provider from contaminants.

The healthcare provider can breathe directly into the input port 72 of the resuscitation attachment 70. Alternatively, a length of flexible tubing 80 can be connected to the resuscitation attachment 70 by means of a connector 82 that can be plugged into the input port 72 of the resuscitation attachment 70, as shown in FIG. 17. In the preferred embodiment, the flexible tubing 80 is approximately six inches in length and forms a helical coil for easier storage. The proximal end of the flexible tubing 80 has a mouthpiece 84 with an oval opening.

The resuscitation attachment 70 can also be equipped with an oxygen port 76, as shown in FIG. 17, that can be connected by tubing to a external oxygen source to supply supplemental oxygen to the patient through the flow path, in addition to the mouth-to-mask resuscitation provided by the healthcare provider. Each exhalation by the healthcare provider then carries oxygen-enriched air through the face mask 20 and into the patient's lungs. The oxygen port 76 can be closed with a removable cap 77 when the oxygen port 76 is not in use. The internal passageway within the flexible tubing 80 and resuscitation attachment 70 upstream from the one-way valve 75 serve as a reservoir for accumulation of oxygen between each exhalation by the healthcare provider.

FIG. 18 shows an alternative embodiment of the resuscitation attachment 70 with the oxygen port 76 placed below the one-way valve 75 and filter 74. In this embodiment, the internal passageway within the resuscitation attachment 70 downstream from the one-way valve 75 serves as a reservoir for accumulation of oxygen between each exhalation by the healthcare provider. The one-way valve 75 helps to prevent oxygen from escaping during the remainder of the resuscitation cycle. However, the exhalation port 73 prevents the build-up of excessive pressure that might be injurious to the patient's lungs.

The above disclosure sets forth a number of embodiments of the present invention. Other arrangements or embodiments, not precisely set forth, could be practiced under the teachings of the present invention and as set forth in the following claims.

I claim:

1. An apparatus for simultaneous resuscitation of a patient by a health care provider while guiding insertion of an endotracheal tube into the trachea of the patient, said apparatus comprising:

a face mask to cover a patient's mouth having:
 (a) a face mask port;
 (b) a ventilation port allowing a flow of air/oxygen into said face mask; and
 (c) a rotatable ventilation collar surrounding said face mask port and directing said flow of air/oxygen from said ventilation port into said face mask, thereby permitting said ventilation port to be rotated about said face mask port;

a resuscitation attachment removably connected to said ventilation port providing a flow path enabling a health care provider to supply a flow of air/oxygen through said ventilation port to resuscitate the patient, said flow path further including a filter reducing the exchange of contaminants between the patient and the health care provider; and a guide removably extending through said face mask port having a distal portion for insertion into the patient's mouth and hypopharynx; said guide directing insertion of an endotracheal tube into the patient's trachea while resuscitation continues via the resuscitation attachment and ventilation port.

2. The apparatus of claim 1 wherein said guide further comprises a curved distal portion.

3. The apparatus of claim 1 wherein said face mask port is resealable.

4. The apparatus of claim 3 wherein said face mask port further comprises a flexible membrane having a stretchable opening for receiving said guide.

5. The apparatus of claim 1 wherein said guide further comprises a resealable port allowing removable insertion of an endotracheal tube along said guide.

6. The apparatus of claim 5 wherein said guide port further comprises a flexible membrane having a stretchable opening for receiving an endotracheal tube.

7. The apparatus of claim 1 wherein said resuscitation attachment further comprises a one-way valve preventing backflow from said face mask.

8. The apparatus of claim 1 wherein said resuscitation attachment further comprises an oxygen port for supplying supplemental oxygen through said flow path.

9. A method for resuscitating a patient and guiding insertion of an endotracheal tube into the patient's trachea comprising the steps of:

placing a face mask over a patient's mouth, said face mask having a removable guide extending posteriorly from the face mask allowing insertion of an endotracheal tube through the face mask and along the guide into the patient's mouth and hypopharynx, said face mask further having a ventilation port allowing a flow of air/oxygen into the face mask;

connecting a resuscitation attachment to the ventilation port to create a filtered flow pat for a flow of air/oxygen into the face mask;

resuscitating the patient by supplying a flow of air/oxygen from a health care provider through the resuscitation attachment and face mask;

inserting a fiber optic probe through an endotracheal tube;

advancing the fiber optic probe and endotracheal tube along the guide into the patient's trachea while resuscitation continues;

removing the fiber optic probe from the endotracheal tube;

removing the face mask while leaving the endotracheal tube in place within the patient's trachea; and ventilating the patient through the endotracheal tube.

10. The method of claim 9 wherein said fiber optic probe is inserted to a position beyond the patient's larynx.

11. The method of claim 9 wherein said resuscitation attachment further comprises a one-way valve preventing backflow from the face mask.

12. The method of claim 9 wherein said guide further comprises a resealable port at the proximal end of the guide and a curved distal portion.

13. The method of claim 9 wherein said face mask further comprises a resealable port for receiving the guide.

14. An apparatus for simultaneously resuscitating a patient and guiding insertion of an endotracheal tube into the patient's trachea, said apparatus comprising:

a face mask to cover a patient's mouth, said face mask having a face mask port;

a rotatable ventilation collar surrounding said face mask port having a ventilation port for receiving a flow of air/oxygen to resuscitate the patient that can be rotated about said face mask port, said ventilation collar directing said flow from said ventilation port into said face mask;

a resuscitation attachment removably connected to said ventilation port providing a flow path enabling a health care provider to supply a flow of air/oxygen through said ventilation port to resuscitate the patient, said flow path further including a filter reducing the exchange of contaminants between the patient and the health care provider; and a guide removably extending through said face mask port having a distal portion for insertion into a patient's mouth and hypopharynx; said guide directing insertion of an endotracheal tube into the patient's trachea while resuscitation continues via the resuscitation attachment and ventilation port.

15. The apparatus of claim 14 wherein said guide further comprises a curved distal portion.

16. The apparatus of claim 14 wherein said face mask port is resealable.

17. The apparatus of claim 14 wherein said face mask port further comprises a stretchable opening for receiving said guide.

18. The apparatus of claim 14 wherein said resuscitation attachment further comprises a one-way valve preventing backflow from said face mask.

19. The apparatus of claim 14 wherein said resuscitation attachment further comprises an oxygen port for supplying supplemental oxygen through said flow path.

* * * * *